`US006869798B2`

(12) United States Patent
Crews et al.

(10) Patent No.: US 6,869,798 B2
(45) Date of Patent: Mar. 22, 2005

(54) LYTIC REAGENT COMPOSITION FOR LEUKOCYTE DIFFERENTIAL ANALYSIS

(75) Inventors: Harold Richardson Crews, Coral Springs, FL (US); Michael N. Elliott, Fort Lauderdale, FL (US); James Harrison Carter, II, Plantation, FL (US)

(73) Assignee: Clinical Diagnostics Solutions, Inc., Plantation, FL (US)

( * ) Notice: Subject to any disclaimer, the term of this patent is extended or adjusted under 35 U.S.C. 154(b) by 46 days.

(21) Appl. No.: 10/418,196

(22) Filed: Apr. 17, 2003

(65) Prior Publication Data

US 2004/0209377 A1 Oct. 21, 2004

(51) Int. Cl.$^7$ .......................... G01N 31/00; G01N 33/48
(52) U.S. Cl. ............................. 436/10; 436/8; 436/17; 436/18; 436/63; 436/164; 436/166; 435/2; 435/29; 435/39; 252/408.1
(58) Field of Search .................... 436/8, 10, 17, 436/18, 63, 164, 166, 174, 175; 435/2, 29, 39; 252/408.1

(56) References Cited

U.S. PATENT DOCUMENTS

| | | | |
|---|---|---|---|
| 4,308,340 A | * 12/1981 | Walls | .......................... 430/331 |
| 4,617,275 A | 10/1986 | Matsuda et al. | |
| 4,637,986 A | 1/1987 | Brown et al. | |
| 5,389,549 A | * 2/1995 | Hamaguchi et al. | .......... 436/10 |
| 5,510,267 A | 4/1996 | Marshall | |
| 5,817,518 A | * 10/1998 | Li et al. | .......................... 436/63 |
| 5,834,315 A | * 11/1998 | Riesgo et al. | ................. 436/66 |
| 5,843,608 A | * 12/1998 | Li et al. | .......................... 436/63 |
| 6,114,130 A | * 9/2000 | Veriac et al. | .............. 435/7.24 |
| 6,507,400 B1 | 1/2003 | Pina et al. | |

FOREIGN PATENT DOCUMENTS

EP         582736    * 2/1994

* cited by examiner

*Primary Examiner*—Maureen M. Wallenhorst
(74) *Attorney, Agent, or Firm*—Martin Fleit; Paul D. Bianco; Fleit Kain Gibbons Gutman Bongini & Bianco P.L.

(57) ABSTRACT

A lytic reagent composition and the method of use for differential analysis of leukocytes using flow cytometry are disclosed. The lytic reagent composition includes a short chain alkyl oxyethanol, such as 2-methoxyethanol, 2-ethoxyethanol, 2-propoxyethanol, or 2-isopropoxyethanol, in a sufficient amount to preserve leukocytes; a non-lysing nonionic surfactant as a debris solublizer; and an inorganic buffer to maintain pH of the lytic reagent composition in a range from 9.1 to 10.7. The lytic reagent composition is used to lyse red blood cells and preserve leukocytes, as well as used as the sheath reagent for the focus flow measurement. The lytic reagent composition, when used on a flow cytometric analyzer with multiple angle light scatter and light absorbance measurements, enables differentiation of leukocytes into five subpopulations.

31 Claims, 7 Drawing Sheets

LYTIC REAGENT COMPOSITION FOR LEUKOCYTE DIFFERENTIAL ANALYSIS

BACKGROUND OF THE INVENTION

1. Field of the Invention

This invention relates to reagent compositions useful in the flow cytometric analysis of blood cells, particularly related to a lytic reagent composition enabling differentiation of leukocyte into five subpopulations.

2. Prior Art

Examination and analysis of the cellular types and subtypes of human and animal whole blood specimens is an important part of modern healthcare. For example, higher or lower numbers of red blood cells (erythrocytes), white blood cells (leukocytes) and platelets are consistent with diagnosis of certain disease states, as well as useful indicators of recovery from the diseases. Traditionally, these tests have been performed by direct counting and size measurement of the cellular constituents by means of a volume-calibrated glass microscope chamber, or more recently by means of electronic counting of the cellular constituents suspended in a supportive, electrically conductive solution. Determination of white blood cell number has been performed in a similar manner, but direct electronic determination of white blood cell subpopulations has only relatively recently become possible by means of electronic size discrimination analysis.

This latter approach to leukocyte differential analysis has been further improved by use of flow cytometric analysis. In this procedure, blood cells are suspended in a reagent solution and passed through a flow cell and detected by an electro-optical detector. The cells are then classified on the basis of one or more measurable parameters, including cellular volume determination by an impedance method, cellular granularity by an RF conductivity method, light scattering or light absorption. The advantages of this type of flow cytometric system over direct microscopic examination is a much higher throughput of specimen samples and the much larger numbers of cells analyzed per sample, thus improving the counting and sizing statistics and reducing the contribution of non-specific noise.

Analyzers using flow cytometric analysis differentiate and classify leukocyte subpopulations by use of light scatter or by electrical impedance parameters, or both. For proper function and sensitivity of the leukocyte analysis, the more numerous red blood cells in the whole blood specimen are usually removed by chemical lysis in order to reveal the much smaller number of white blood cells. For electrical impedance-based analyzers, stronger lysing reagents, such as quaternary ammonium surfactant based reagents, have been used for differentiating leukocytes into two or three subpopulations by sizing. However, such lysing reagents cause serious leukocyte membrane damage, rendering the differential analysis unsuitable when the blood sample is analyzed by flow cytometric systems employing light scattering and light absorbance measurements. For these types of measurement systems, lytic reagents should provide rapid red cell lysis, but not unduly disturb the light scattering or absorption characteristics of leukocytes for a time long enough to collect optical data for the differential analysis.

It is known that blood cell lysis proceeds more rapidly at alkaline pH than at neutral or acidic pH. Lytic reagents with very alkaline or very acidic pH typically can lyse red blood cells, as well as white blood cells, rendering the leukocyte differential analysis difficult. Reagents with near neutral pH are too slow, requiring several minutes to complete the lysing reaction.

U.S. Pat. No. 4,617,275 (to Matsuda, et al.) describes the use of a lysing reagent comprising quaternary ammonium salts to provide adequate red cell lysis without excessively damaging the white blood cells for the purpose of electrical impedance measurement of at least three subpopulations of leukocytes. The lysing reagent contains citric acid to assist in removal of the interfering red cell ghosts. The analysis method requires the use of a diluent solution as a co-reagent. The diluent contains a buffer comprised of boric acid and sodium borate.

U.S. Pat. No. 4,637,986 (to Brown, et al.) describes a flow cytometry lysing reagent for producing a 3-part differential of leukocytes. The lysing reagent is a hypotonic aqueous solution enabling hypotonic lysis of red blood cells. The lysing reagent comprises a leukoprotective agent for preserving the lymphocyte cellular integrity during analysis, and buffers to provide the correct pH environment for optimal lysis. The preferred leukoprotective agents include methyl oxyethanol, ethyl oxyethanol and butyl oxyethanol. Brown et al. specifically teach the importance of the pH range of the lysing reagent in order to provide rapid lysing of red blood cells, but prevent deterioration of the leukocytes. More specifically, the preferred pH range is from approximately 8.1 to about 8.8, with optimal around 8.5. Brown et al. teach that if pH of the lysing reagent is above 9.0, a rapid deterioration of the white blood cells occurs, which results in disadvantageous effects on counting accuracy. Furthermore, Brown et al. teach that the specific buffering agent is critical to the proper operation of the lysing agent. More specifically, it is found that mineral buffers such as phosphate and carboxylic acids or molecules containing a carboxyl group are not effective, and the boric acid/TRIS buffer combination is also less effective. Brown et al. specifically teach the optimal buffer system of an organic, nitrogen containing buffer balanced with an ethane sulfonic acid buffer to maintain pH of the lysing reagent from 8.1 to 8.8.

U.S. Pat. No. 5,510,267 (to Marshall) describes a flow cytometry lytic reagent and a method for providing a 5-part differential analysis of leukocytes. The method includes diluting a blood sample with a neutral and near isotonic diluent, mixing the diluted sample with the lytic reagent to lyse red blood cells, and analyzing the sample mixture in a flow cell by measuring 0°, 10°, 90° and 90° depolarized light scatter signals to differentiate leukocytes into five subpopulations, including neutrophils, lymphocytes, monocytes, eosinophils and basophils. Marshall teaches that the lytic reagent includes 2-phenoxyethanol which combines the function of leukoprotective and antimicrobial; Triton X-100 (octylphenoxypolyethoxyethanol) a lytic and wetting agent; and an organic buffer with pKa at or near 8.5 to maintain pH of the lysing reagent at 8.5. Furthermore, Marshall teaches the importance of pH to the function of the lytic reagent. More specifically, the optimal pH is 8.5, and with a lower range of 8.1 without significant effects on the reagent performance. However, if pH of the lytic reagent increases to 9.0, partial destruction of white blood cells can occur.

Both U.S. Pat. No. 4,637,986 and U.S. Pat. No. 5,510,267 teach that red blood cell lysis under alkaline condition is more rapid, which is desirable for automated hematology analyzers. However, at pH above 9, white blood cell damage occurs, which impacts the accuracy of the leukocyte counting and differential analysis.

Therefore, it is apparent that there is a need for an improved lytic reagent composition which enables rapid red blood cell lysis under alkaline condition, but enables preserving the leukocytes for leukocyte differential analysis using automated hematology analyzers.

SUMMARY OF THE INVENTION

In one aspect, the present invention provides a lytic reagent composition for differential analysis of leukocytes using optical measurements. The lytic reagent composition comprises a short chain alkyl oxyethanol selected from the group consisting of 2-methoxyethanol, 2-ethoxyethanol, 2-propoxyethanol, and 2-isopropoxyethanol in a sufficient amount to preserve leukocytes; a non-lysing nonionic surfactant as a debris solublizer; and an inorganic buffer to maintain pH of the lytic reagent composition in a range from about 9.1 to about 10.7.

The inorganic buffer includes disodium tetraborate decahydrate, dipotassium tetraborate decahydrate, sodium carbonate, sodium bicarbonate, disodium phosphate, dipotassium phosphate, trisodium phosphate, and tripotassium phosphate.

The non-lysing nonionic surfactant includes polyoxyethylene nonylphenol having from about 30 to about 60 ethylene oxide groups, polyoxyethylene octylphenol having from about 30 to about 60 ethylene oxide groups, polyethoxyethylene phosphates having from about 30 to about 80 ethylene oxide groups, and polyoxyethyelene-polyoxypropylene block copolymers having from about 30 to about 150 ethylene oxide groups and at least 2 propylene oxide groups.

The lytic reagent composition further comprises an antimicrobial to inhibit the growth of bacteria and fungi.

The lytic reagent composition of the present invention enables a rapid lysis of red blood cells in blood sample and preservation of leukocytes of their light scatter and light absorbance characteristics for the period of time required for optical measurements on an automated hematology analyzer.

In another aspect, the present invention provides a method of differentiating leukocytes into five subpopulations using the lytic reagent composition of the present invention and flow cytometric measurement. The method comprises the steps of mixing a blood sample with the lytic reagent composition of the present invention to lyse red blood cells, measuring axial light absorbance and multiple angles of light scatter signals of the cells passing through a focused flow cell, and analyzing the measured optical signals to differentiate leukocytes into five subpopulations, including lymphocytes, monocytes, granulocytes, eosinophils and basophils.

The lytic reagent composition for differential analysis of leukocytes according to the present invention comprises a short chain alkyl oxyethanol selected from the group consisting of 2-methoxyethanol, 2-ethoxyethanol, 2-propoxyethanol, and 2-isopropoxyethanol in a sufficient amount to preserve leukocytes; a non-lysing nonionic surfactant as a debris solublizer; and an inorganic buffer to maintain pH of said lytic reagent composition in a range from about 9.1 to about 10.7.

The inorganic buffer can be selected from the group consisting of disodium tetraborate decahydrate, dipotassium tetraborate decahydrate, sodium carbonate, sodium bicarbonate, disodium phosphate, dipotassium phosphate, trisodium phosphate, and tripotassium phosphate, and is preferably disodium tetraborate decahydrate in amount sufficient to maintain pH of said lytic reagent from about 9.1 to about 10.7.

The short chain alkyl oxyethanol is preferably 2-propoxyethanol, is in a concentration range from about 0.003% to about 1% (w/v).

The non-lysing nonionic surfactant is one selected from the group consisting of polyoxyethylene nonylphenol having from about 30 to about 60 ethylene oxide groups, polyoxyethylene octylphenol having from 30 to about 60 ethylene oxide groups, polyethoxyethylene phosphates having from 30 to about 80 ethylene oxide groups, and polyoxyethylene-polyoxypropylene block copolymer having from about 30 to about 150 ethylene oxide groups and at least 2 propylene oxide groups.

The non-lysing nonionic surfactant is preferably polyoxyethylene nonylphenol having from about 30 to about 60 ethylene oxide groups, and preferably is in a concentration range from about from about 0.003% to about 1% (w/v). The lytic reagent composition can further including an antimicrobial.

In a preferred embodiment, the lytic reagent composition for differential analysis of leukocytes consists essentially of:

a. 2-propoxyethanol in a sufficient amount to preserve leukocytes;

b. polyoxyethylene nonylphenol having from about 30 to about 60 ethylene oxide group; and c. an inorganic buffer to maintain pH of said lytic reagent composition in a range from about 9.1 to about 10.7.

In the preferred embodiment noted in the preceding paragraph, the inorganic buffer is selected from the group consisting of disodium tetraborate decahydrate, dipotassium tetraborate decahydrate, sodium carbonate, sodium bicarbonate, disodium phosphate, dipotassium phosphate, trisodium phosphate, and tripotassium phosphate, and preferably, said inorganic buffer is disodium tetraborate decahydrate. Also, said 2-propoxyethanol is in a concentration range from about from about 0.003% to about 1% (w/v). Further, said polyoxyethylene nonylphenol having from about 30 to about 60 ethylene oxide group is in a concentration range from about from about 0.003% to about 1% (w/v). In addition, the lytic reagent composition can further including an antimicrobial.

As noted above, the novel lytic reagent composition for differential analysis of leukocytes comprises: a short chain alkyl oxyethanol selected from the group consisting of 2-methoxyethanol, 2-ethoxyethanol, 2-propoxyethanol, and 2-isopropoxyethanol in a sufficient amount to preserve leukocytes; a non-lysing nonionic surfactant as a debris solublizer; and an inorganic buffer to maintain pH of said lytic reagent composition in a range from about 9.1 to about 10.7; wherein said lytic reagent composition enables differentiation of leukocytes into five subpopulations by optical measurements. The said five leukocyte subpopulations can include neutrophils, lymphocytes, monocytes, eosinophils and basophils. Further, said optical measurements comprises multiple angle light scatter measurements and light absorbance measurement. Also, said multiple angle light scatter measurements includes light scatter measurements at from 0° to about 30°, from about 30° to about 50°, and from about 50° to about 90°. Said light absorbance measurement is preferably axial light absorbance measurement.

As noted above said inorganic buffer is selected from the group consisting of disodium tetraborate decahydrate, dipotassium tetraborate decahydrate, sodium carbonate, sodium bicarbonate, disodium phosphate, dipotassium phosphate, trisodium phosphate, and tripotassium phosphate. Said inorganic buffer is preferably disodium tetraborate decahydrate.

In the lytic reagent composition noted above, said short chain alkyl oxyethanol is 2-propoxyethanol, and is in a concentration range from about from about 0.003% to about 1% (w/v); said non-lysing nonionic surfactant is one selected from the group consisting of polyoxyethylene nonylphenol having from about 30 to about 60 ethylene oxide groups, polyoxyethylene octylphenol having from 30 to about 60 ethylene oxide groups, polyethoxyethylene phosphates having from 30 to about 80 ethylene oxide groups, and polyoxyethylene-polyoxypropylene block copolymer having from about 30 to about 150 ethylene oxide groups and at least 2 propylene oxide groups; and said non-lysing nonionic surfactant is polyoxyethylene nonylphenol having from about 30 to about 60 ethylene oxide group and is in a concentration range from about from about 0.003% to about 1% (w/v). The lytic reagent composition can further comprise an antimicrobial.

The method for differential analysis of leukocytes using flow cytometry comprising the step of using as a lytic reagent composition for differential analysis of leukocytes, the composition comprising: (a) a short chain alkyl oxyethanol selected from the group consisting of 2-methoxyethanol, 2-ethoxyethanol, 2-propoxyethanol, and 2-isopropoxyethanol in a sufficient amount to preserve leukocytes; (b) a non-lysing nonionic surfactant as a debris solublizer; and (c) an inorganic buffer to maintain pH of said lytic reagent composition in a range from about 9.1 to about 10.7; wherein said lytic reagent composition enables differentiation of leukocytes into five subpopulations by optical measurements.

Other objects and advantages of the present invention will become more apparent from the following detailed description of preferred embodiments when taken with the appended drawings.

BRIEF DESCRIPTION OF THE DRAWINGS

FIGS. 3A to 3F illustrate a comparison of leukocyte differential analysis results obtained comparing the composition of the present invention and a commercial composition, in this instance, Bayer Advia 70 with respect to a group of blood samples that were run on the same machine (the Danam EXCELL 22 hematology blood analyzer or Bayer Advia 70 hematology analyzer) using the two compositions.

DETAILED DESCRIPTION OF PREFERRED EMBODIMENTS OF THE INVENTION

In one embodiment, the present invention is related to an aqueous lytic reagent composition for differential analysis of leukocytes using light scatter and light absorption measurement in a focused flow cell. The lytic reagent composition comprises a short chain alkyl oxyethanol in a sufficient amount to preserve leukocytes; a non-lysing nonionic surfactant as a debris solublizer; and an inorganic buffer to maintain pH of the lytic reagent composition in a range from about 9.1 to about 10.7. The lytic reagent is hypotonic and has an osmolality in a range from about 25 mOsm to about 150 mOsm.

When a blood sample, such as a peripheral whole blood sample, is mixed with a sufficient amount of lytic reagent of the present invention, the red blood cells are lysed rapidly by osmotic shock in the aqueous solution under an alkaline condition, while the leukocytes remain in the sample mixture for a subsequent optical differential analysis on an automated instrument.

Selection of a buffering material and appropriate pH range is important for the optimal performance of the lytic reagent. At neutral pH, lysis of the red blood cells is too slow to be suitable for the throughput requirement of an automated blood analyzer. On the other hand, under extreme alkaline pH, such as at pH 11 or higher, substantial damage of the leukocytes occurs, which can render the differential analysis of leukocyte subpopulations difficult.

It has been found that with the lytic reagent composition of the present invention, a pH range from about 9.1 to about 10.7 provides the balance of the desired rapid lysis of red blood cells and preservation of leukocytes. More preferably, the pH range is from about 9.3 to about 9.9. Either inorganic or organic buffers having pKa around 9.3 to 9.9 can be used. However, inorganic buffers were preferably selected because of their inherently stronger buffering action versus most organic buffers, which permits a low buffer concentration desired for rapid hypotonic lysis. Furthermore, inorganic buffers are in general less costly than organic buffers.

Suitable inorganic buffers for maintaining the lytic reagent in the desired alkaline condition include disodium tetraborate decahydrate, dipotassium tetraborate decahydrate, sodium carbonate, sodium bicarbonate, disodium phosphate, dipotassium phosphate, trisodium phosphate, and tripotassium phosphate. The amount of an inorganic buffer is sufficient to maintain pH of the lytic reagent from about 9.1 to about 10.7, and preferably from about 9.3 to about 9.9. In a preferred embodiment, disodium tetraborate decahydrate in a concentration from about 0.003% to about 1% (w/v, weight by volume) is used.

It is important to preserve the leukoctyes under a lysing condition to prevent damage of the leukocytes and undesired changes of their optical properties. It has been found that under hypotonic lysing condition and alkaline pH, alkyl oxyethanol compounds with alkyl carbon chain lengths up to about three carbons, hereinafter referred as short chain alkyl oxyethanols, function as an effective leukoprotective agent. The short chain alkyl oxyethanol retards lysis of leukocytes, and preserves optical properties of leukocyte subpopulations during the optical differential analysis of the sample mixture. On the other hand, the short chain alkyl oxyethanol does not inhibit hypotonic lysis of red blood cells. When the alkyl chain further lengthens, such as four-carbon chain in butyloxy-ethanols, poor solubility of these compounds in aqueous solution becomes undesirable.

The short chain alkyl oxyethanols suitable for the lytic reagent of the present invention include 2-methoxyethanol, 2-ethoxyethanol, 2-propoxyethanol, and 2-isopropoxyethanol. In a preferred embodiment, 2-propoxyethanol in a concentration range from about 0.003% to about 1% (w/v) is used.

Red blood cell debris in the described sample mixture can be a concern for a subsequent optical measurement. The presence of substantial amount of red blood cell debris can interfere with counting as well as differential analysis of leukocytes. Because the debris above the counting threshold for leukocytes can reduce the proportion of leukocytes counted during the measurement, thus it can reduce accuracy of the counting and the differentiation. It has been found that a low concentration of a non-lysing nonionic surfactant can be used in the lytic reagent of the present invention to reduce the amount of red blood cell debris, functioning as a debris solublizer. Herein the term of non-lysing nonionic surfactant means that the nonionic surfactant at the concentration used does not cause lysis of red blood cells during the time period required for the blood analysis.

Suitable examples of the non-lysing nonionic surfactants include polyoxyethylene nonylphenol having from about 30 to about 60 ethylene oxide groups, polyethoxyethylene phosphates having from about 30 to about 80 ethylene oxide groups, polyoxyethylene octylphenol having from about 30 to about 50 ethylene oxide groups, and polyoxyethylene-polyoxypropylene block copolymers having from about 30 to about 150 ethylene oxide groups and at least 2 propylene oxide groups. Preferably, polyoxyethylene nonylphenol having from about 35 to about 50 ethylene oxide groups is used. Most preferably, polyoxyethylene nonylphenol having about 40 ethylene oxide groups, such as TRYCOL 6970, manufactured by Cognis Corp., Cleveland, Ohio, in a concentration range from about 0.003% to 1% (w/v) is used.

The lytic reagent composition further comprises an antimicrobial for preserving the lytic reagent and providing a sufficient shelf life of the lytic reagent product. The antimicrobial is in a sufficient amount to inhibit the growth of bacterial and fungal microorganisms, but not interfere with the function of active ingredients and performance of the lytic reagent for the desired blood analysis. For the purpose of the present invention, the preservative should be effective at very low concentrations, and preferably non-ionic to prevent undesirable increases in reagent osmolality, and also be non-lytic to white blood cells. To achieve a strong effect, more than one antimicrobial preservative compounds, such as mixtures of 5-chloro-2-methyl-4-isothiazolin-3-one and 2-methyl-4-isothiazolin-3-one, or hexahydro-1,3,5-tris (hydroxyethyl)-s-triazine can be utilized. A suitable example of antimicrobial is hexahydro 1,3,5-tris (2-hydroxyethyl)-s-triazine, available commercially as Surcide P, manufactured by Surety Laboratories Inc at Cranford N.J. Surcide P can be used in a concentration range from about 0.008% to about 0.25% (w/v).

The lytic reagent composition of the present invention can be used on several automated hematology analyzers which perform leukocyte differential analysis using optical measurements. The examples include Danam EXCELL 22, manufactured by Danam-MWI, Dallas Tex.; Bayer Advia 70, manufactured by Bayer Diagnostics, Tarrytown N.Y.; Abbott Cell-Dyn 3000, 3500 and 3700, manufactured by Abbott Laboratories, Abbott Park, Ill.

In general, an aliquot of a blood sample is aspirated on an automated haematology analyzer, and mixed with a predetermined volume of the lytic reagent of the present invention to form a sample mixture. The dilution ratio between the blood sample and the lytic reagent can be instrument dependent, generally in a range from about 1:30 to about 1:60. Upon reaction with the lytic reagent, the red blood cells are lysed, and remaining leukocytes are suspended in the sample mixture that is delivered to a focused flow cell for optical measurement. The light scatter signals and axial light absorbance of a single cell passing through the flow cell are detected at various light scatter angles (instrument dependent) by optical detectors. The acquired light scatter and absorbance signals from thousands of individual cells are then transformed into one or more two dimensional scattergrams which display distribution of subpopulations of leukocytes. A differential analysis is performed using these optical parameters to differentiate leukocytes into five subpopulations, including lymphocytes, monocytes, neutrophils, eosinophils and basophils.

The lytic reagent of the present invention is particularly suitable for the Danam EXCELL 22 hematology blood analyzer (Danam-MWI, Dallas, Tex.). On the Danam EXCELL 22, an aliquot of blood sample is mixed with the lytic reagent of the present invention with a dilution ration of 1:40. The sample mixture is injected, hydrodynamcially focused, into the flow cell. Hydrodynamic focusing creates a monofile of cells surrounded by a sheath reagent, flowing in the center of the channel of the flow cell. As the cells pass through the laser beam focused at the flow cell, the cells scatter light in unique patterns dependent on their size and structures. In addition, they absorb some of the light energy. The axial light absorbance and light scatter signals of the sample mixture are measured in the flow cell. The light scatter signals are measured at several angles, including a forward angle (FS, from about 0° to about 30°), and wide angle (WA, from about 30° to about 50°) and a super wide angle (SWA, from about 50° to about 90°). These optical signals are transformed and displayed in two scattergrams. The first scattergram has the forward scatter as the Y axis, and wide angle scatter as the X axis. In this scattergram, four clusters, lymphocytes, monocytes, basophils and a cluster containing neutrophils and eosinophils can be readily identified. The second scattergram has the super wide angle scatter as the Y axis, and extinction or absorbance (EX) as the X axis. In the second scattergram, the eosinophils are an isolated cluster above the other leukocyte subpopulations. Enumeration of each cluster in these two scattergrams permits calculation of the relative percentage of each leukocyte subpopulation.

Furthermore, the time stamp on each cell data permits the development of a counting rate histogram. A least squares regression yields a line slope and intercept. The intercept when multiplied by a calibration constant is indicative of the WBC optical count (WOC).

From the above-described blood analysis, the Danam EXCELL 22 reports percentages of five subpopulations including lymphocytes, monocytes, neutrophils, eosinophils and basophils, and WBC optical count (WOC) of the blood sample. Absolute count of each subpopulation can be obtained by multiplying the percentage of each subpopulation with WOC.

The lytic reagent composition of the present invention can be used as the lytic reagent and as the sheath reagent on Danam EXCELL 22. The sheath reagent is used for providing hydrodynamic focusing. Using the same reagent for lysing and as sheath has the advantage to minimize the refraction index difference between the sample mixture suspension flowing through the center of the flow cell and the surrounding sheath, which is beneficial for optical measurement. However, the lytic reagent of the present invention can also be used with other suitable sheath reagents.

Figure 1:
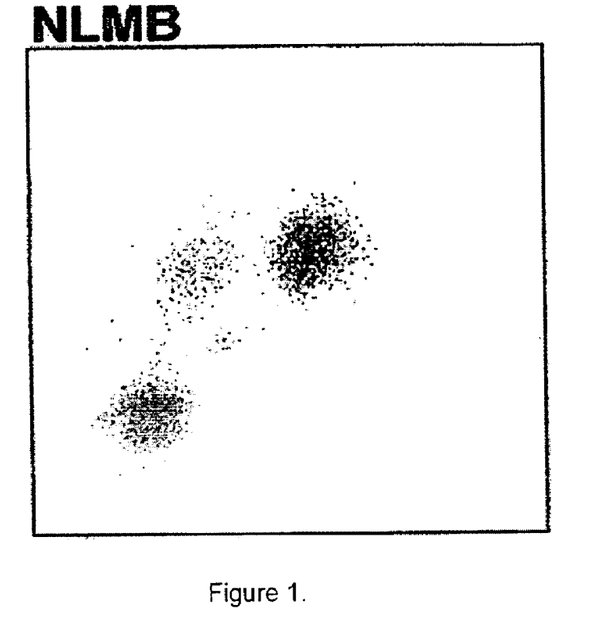
FIG. 1 is a scattergram showing four clusters of leukocyte subpopulations resulting from the use of the novel inventive composition.
Figure 2:
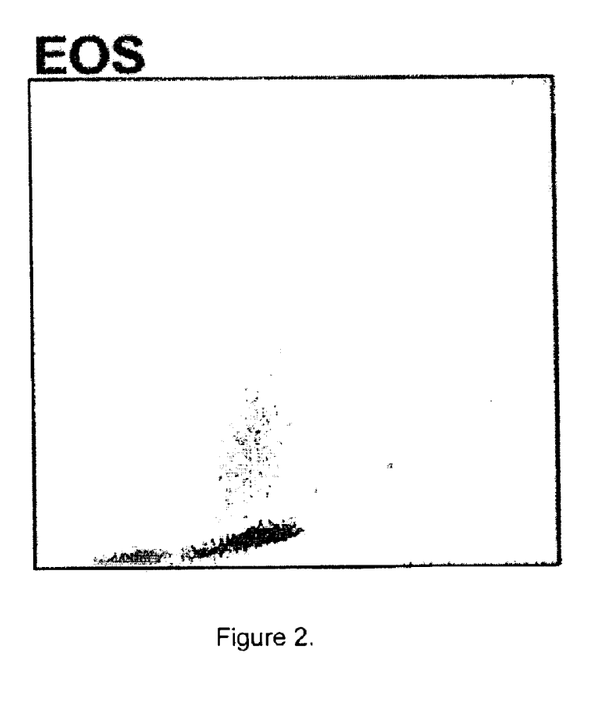
FIG. 2 is a scattergram derived from the scattergram of FIG. 1 showing the eosinphil cluster subpopulation in a SWA (super wide angle) vs EX (extinction).

In Examples 1 and 2, two lytic reagent compositions of the present invention are described. Example 3 illustrated the leukocyte differential analysis result of a whole blood sample obtained using the lytic reagent composition of Example 1 on a Danam EXCELL 22 analyzer. As shown in FIG. 1, four clusters of leukocyte subpopulations of a blood sample are differentiated in the FS vs WA scattergram. FIG. 2 shows that the eosinophil cluster is clearly isolated from other subpopulations in the SWA vs EX scattergram.

Figure 3A:
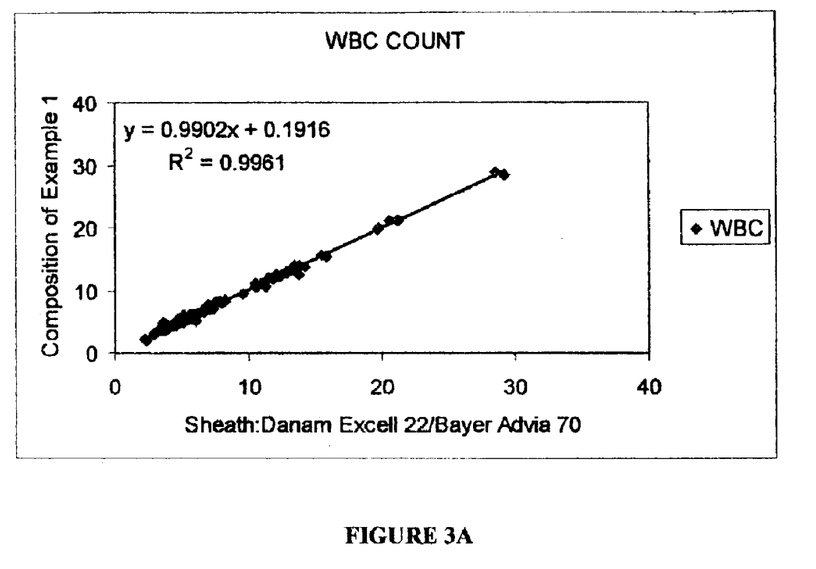
FIG. 3A shows a comparative chart of white blood count (in 1000s)
Figure 3B:
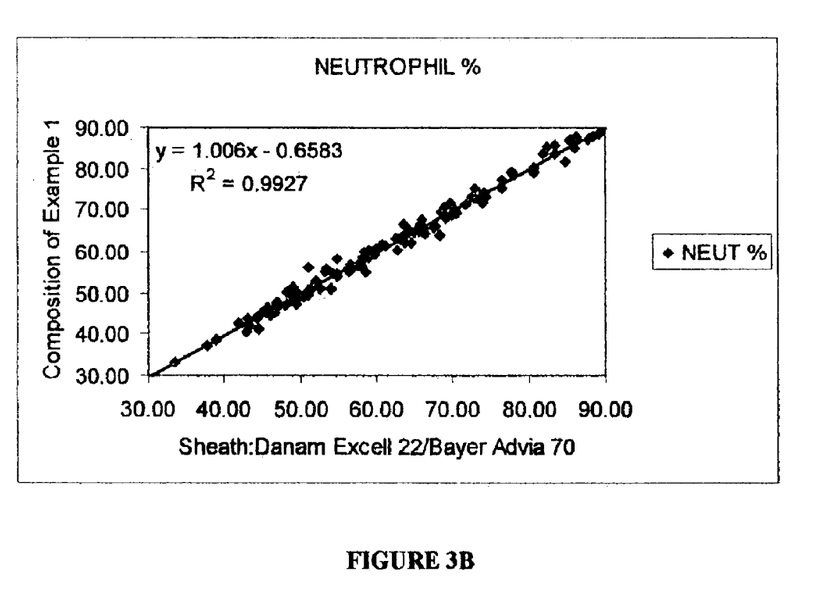
FIGS. 3B to 3F show similar charts for neutrophils %, lymphocyte %, monocytes %, eosinophil %, and basophil %.
Figure 3C:
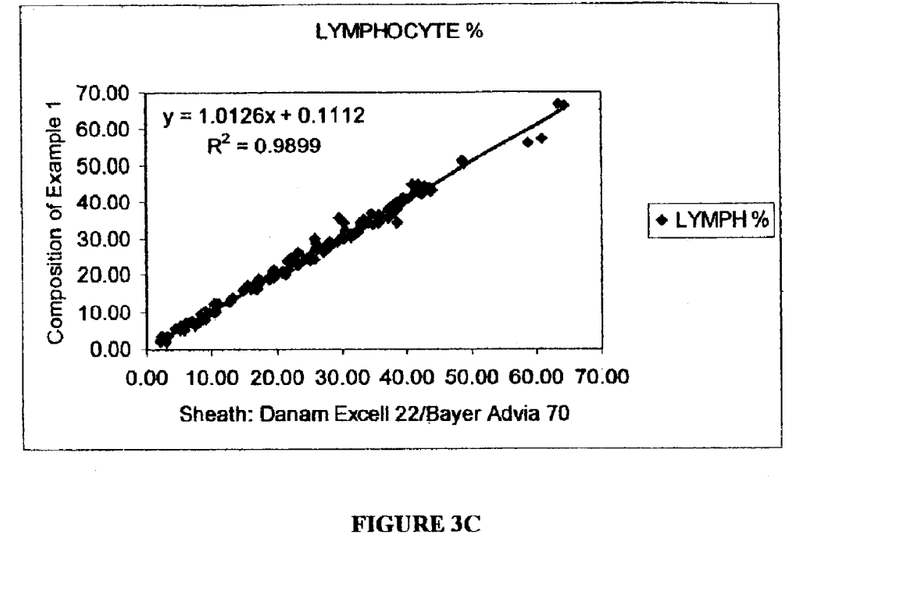
Figure 3D:
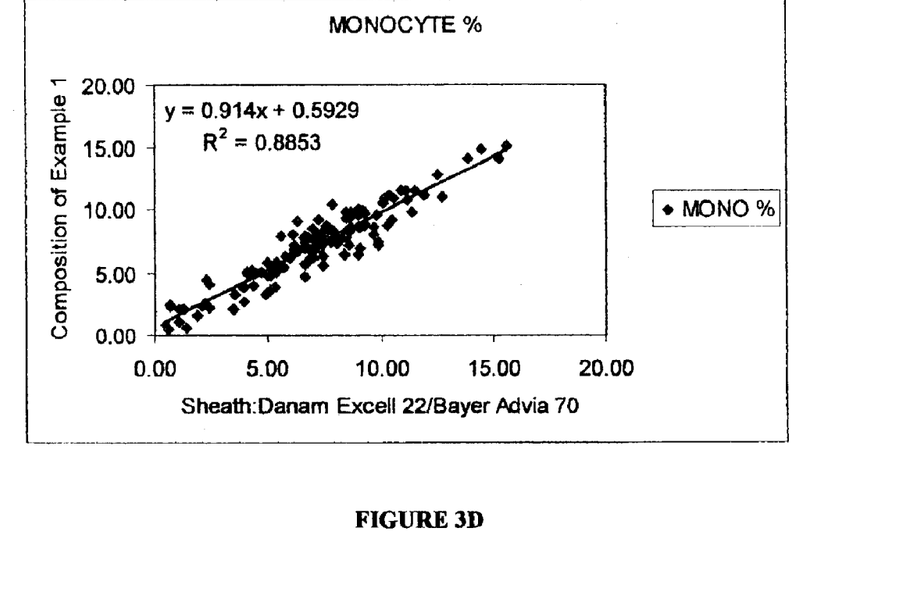
Figure 3E:
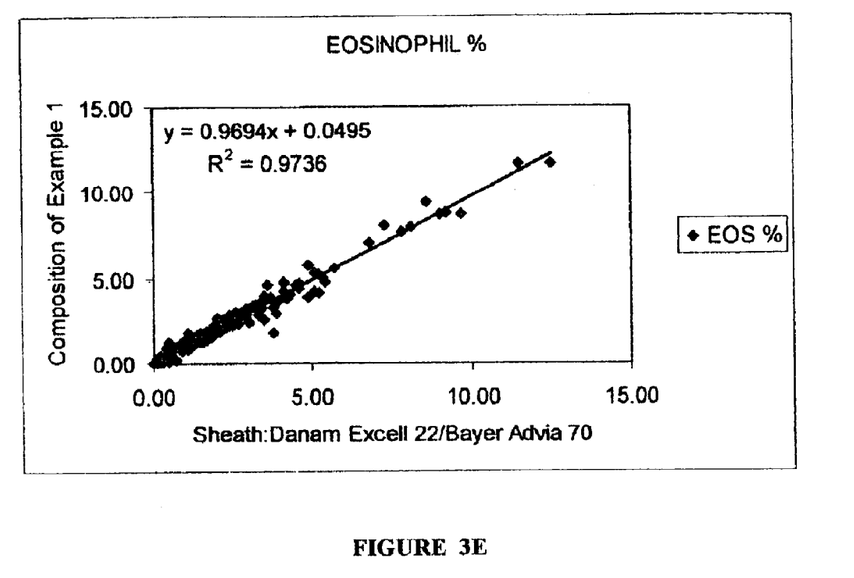
Figure 3F:
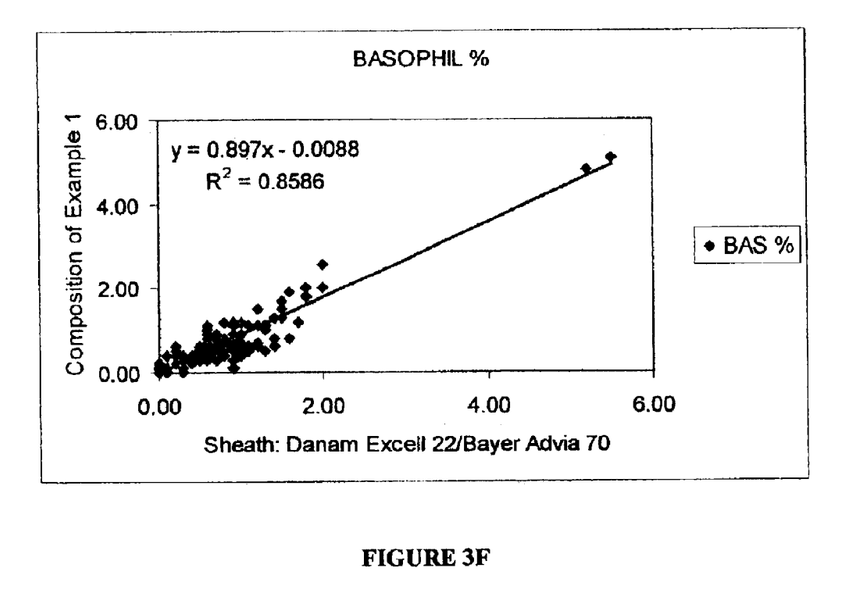

Example 4 illustrated a comparison of the leukocyte differential analysis results obtained on a Bayer Advia 70 hematology analyzer using the lytic reagent composition described in Example 1 and using a commercial product Bayer Advia 70 sheath, manufactured by Bayer Diagnostics, Tarrytown, N.Y. As shown in FIGS. 3A–3E, WBC count, and percentages of neutrophils (Neut%), Lymphocytes (Lymph%), monocytes (Mono%) and eosinophils (Eos%) obtained from the lytic reagent of the present invention have an excellent correlation to those obtained using Bayer Advia 70 sheath. As shown in FIG. 3F, the percentage of basophils (Baso%) obtained from the lytic reagent of the present invention has a good correlation to that obtained using Bayer Advia 70 sheath.

Figure 4A:
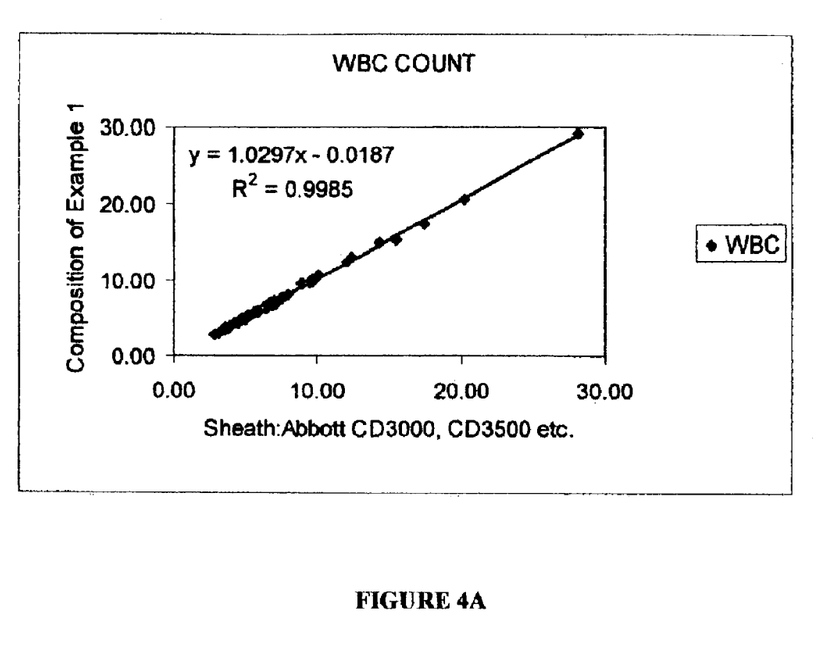
FIGS. 4A to 4F are similar to and correspond to FIGS. 3A to 3F, with the difference being that in these charts the composition of the present invention is being compared with a commercial composition, in this instance, Sheath Abbott Cell Dyn 3500, and the hematology analyzer is the Abbott Cell-Dyn 3500 hematology analyzer.
Figure 4B:
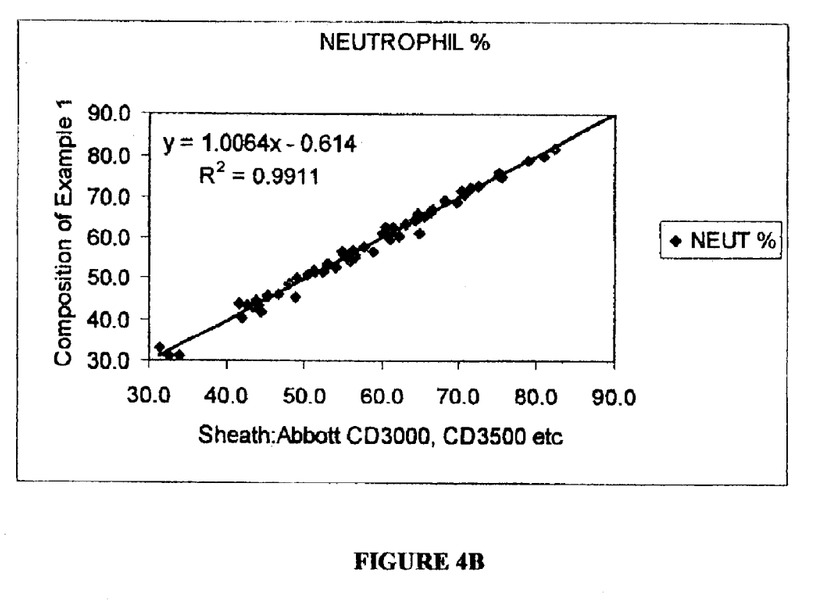
Figure 4C:
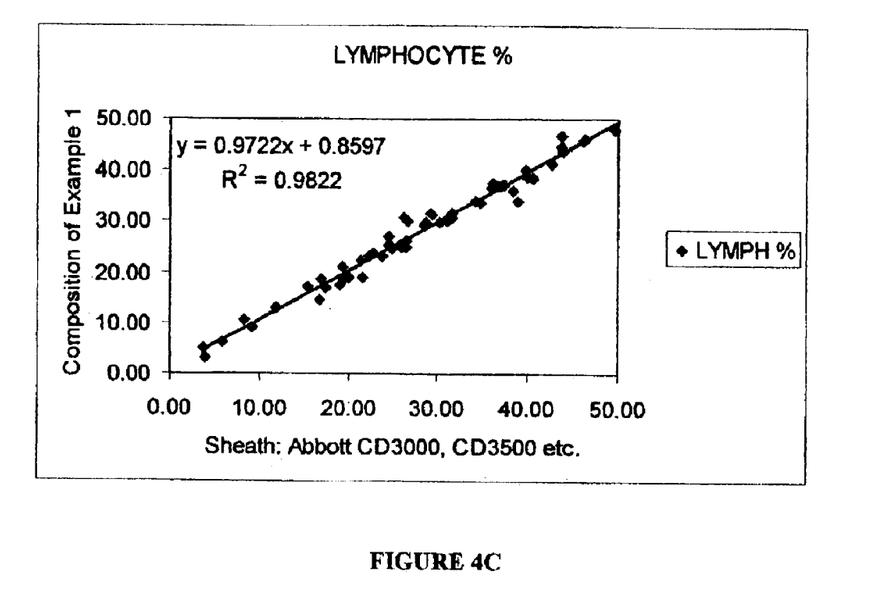
Figure 4D:
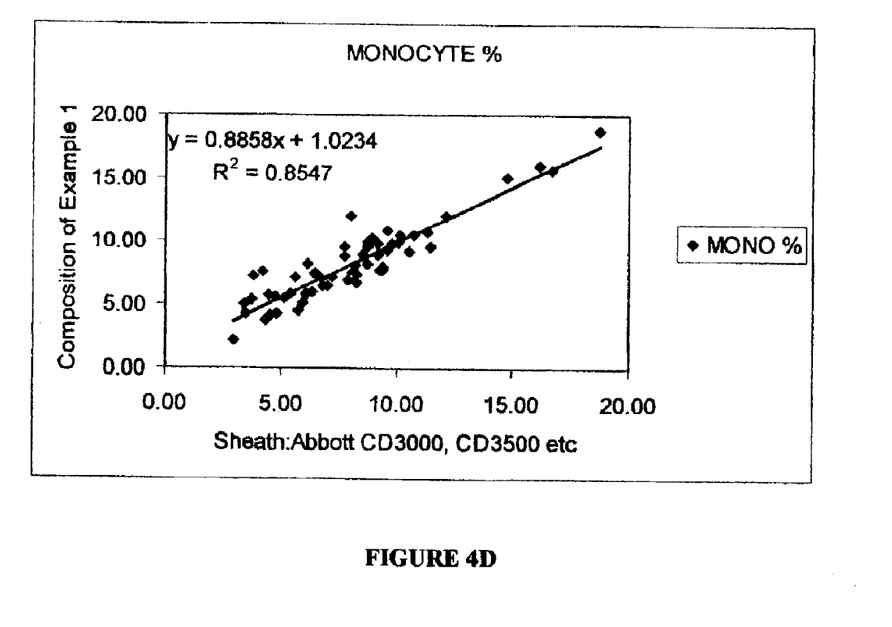
Figure 4E:
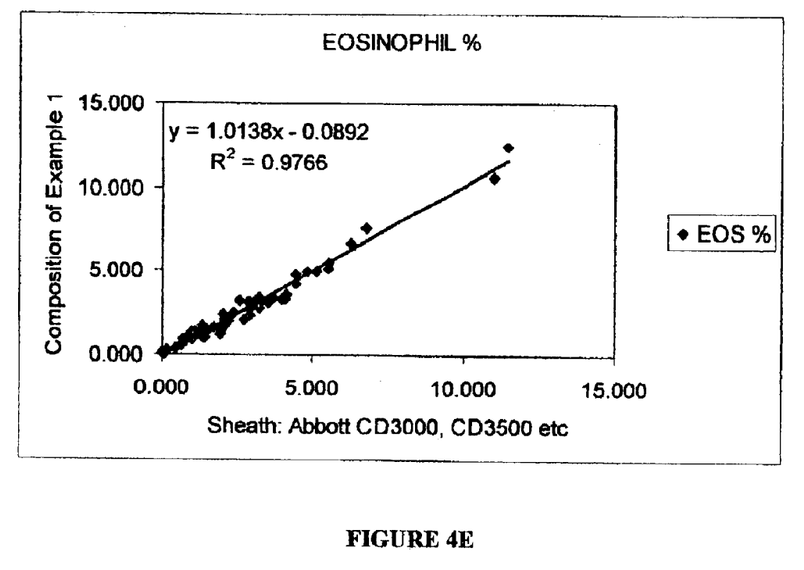
Figure 4F:
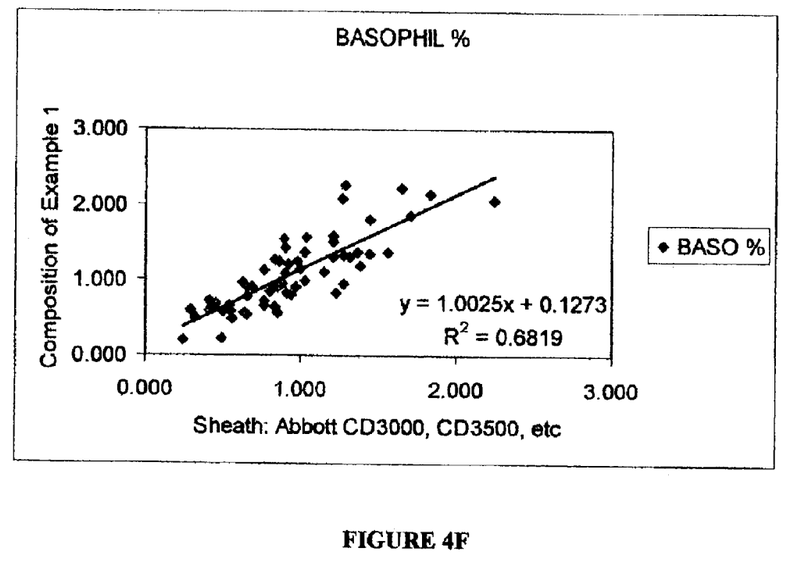

Example 5 illustrated a comparison of the leukocyte differential analysis results obtained on a Abbott Cell-Dyn 3500 hematology analyzer using the lytic reagent composition described in Example 1 and using a commercial product Sheath Abbott Cell Dyn 3500 etc, manufactured by Abbott Laboratories, Abbott park, N.Y. As shown in FIGS. 4A–4C and 4E, WBC count, and percentages of neutrophils (Neut%), Lymphocytes (Lymph%), eosinophils (Eos%) obtained from the lytic reagent of the present invention have an excellent correlation to those obtained using Sheath Abbott Cell Dyn 3500 etc. As shown in FIGS. 4D and 4F, the percentages of monocytes (Mono%) and basophils (Baso%) obtained from the lytic reagent of the present invention have a good correlation to those obtained using Sheath Abbott Cell Dyn 3500 etc.

EXAMPLE 1

A lytic reagent composition was prepared as follows:

| | |
|---|---|
| 2-propoxy-ethanol | 2.00 g/L |
| Sodium tetraborate decahydrate | 1.00 g/L |
| Trycol 6970 (Cognis Corp) | 1.10 g/L |
| Surcide-P | 1.15 g/L |
| D.I. water | QA to 1 liter | pH of the lytic reagent is from 9.5
Osmolality of the lytic reagent is from 45

EXAMPLE 2

A lytic reagent composition was prepared as follows:

| | |
|---|---|
| 2-propoxy-ethanol | 2.00 g/L |
| Sodium Phosphate Dibasic | 1.40 g/L |
| Pluronic F68 | 2.0 g/L |
| Surcide-P | 1.15 g/L |
| D.I. water | QA to 1 liter | pH of the lytic reagent is 9.8
Osmolality of the lytic reagent is 46 mOsm
Wherein Pluronic F68 is a polyoxyethylene-polyoxypropylene block copolymer having 100–150 ethylene oxide groups and at least 2 propylene oxide groups, which is manufactured by BASF, Mount Olive, N.J.

EXAMPLE 3

A whole blood sample is analyzed on a Danam EXCELL 22 hematology analyzer according to the procedure described in the manufacturer's operator manual using the lytic reagent composition described in Example 1. FIGS. 1 and 2 illustrate the obtained FS vs WA and SWA vs EX scattergrams, respectively.

EXAMPLE 4

63 whole blood samples, including 20 normal blood samples and 43 clinical blood samples, were analyzed on a Bayer Advia 70 hematology analyzer according to the procedure described in the manufacturer's operator manual using Bayer Advia 70 sheath manufactured by Bayer Diagnostics. Then Bayer Advia 70 sheath was replaced by the lytic reagent composition of the present invention described in Example 1, and the same blood samples were analyzed again on the analyzer according to the same procedure. A correlation of the reported WBC, percentage of neutrophils (Neut %), Lymphocytes (Lymph %), monocytes (Mono %). eosinophils (Eos %), and basophils (Baso %), between the two described lytic reagents, is shown in FIG. 3A to 3F, respectively.

EXAMPLE 5

140 whole blood samples, including 50 normal blood samples and 90 clinical blood samples, were analyzed on an Abbott Cell-Dyn 3500 hematology analyzer according to the procedure described in the manufacturer's operator manual using Sheath Abbott Cell Dyn 3500 etc, manufactured by Abbott laboratories. Then the Abbott Cell Dyn 3500 sheath etc was replaced by the lytic reagent composition of the present invention described in Example 1, and the same blood samples were analyzed again on the analyzer according to the same procedure. A correlation of the reported WBC, percentage of neutrophils (Neut %), Lymphocytes (Lymph %), monocytes (Mono %), eosinophils (Eos %) and basophils (Baso %), between the two described lytic reagents, is shown in FIGS. 4A to 4F, respectively.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. The method for differential analysis of leukocytes using flow cytometry comprising the step of using as a lytic reagent composition for differential analysis of leukocytes, the composition comprising:

(a) a short chain alkyl oxyethanol selected from the group consisting of 2-methoxyethanol, 2-ethoxyethanol, 2-propoxyethanol, and 2-isopropoxyethanol in a sufficient amount to preserve leukocytes;

(b) a non-lysing nonionic surfactant as a debris solublizer; and (c) an inorganic buffer to maintain pH of said lytic reagent composition in a range from about 9.1 to about 10.7;

wherein said lytic reagent composition enables differentiation of leukocytes into subpopulations by optical measurements.

2. A method according to claim 1, wherein said inorganic buffer is selected from the group consisting of disodium tetraborate decahydrate, dipotassium tetraborate decahydrate, sodium carbonate, sodium bicarbonate, disodium phosphate dipotassium phosphate, trisodium phosphate, and tripotassium phosphate.

3. A method according to claim 2, wherein said inorganic buffer is disodium tetraborate decahydrate in amount sufficient to maintain pH of said lytic reagent from about 9.1 to about 10.7.

4. A method according to claim 1, wherein said short chain alkyl oxyethanol is 2-propoxyethanol.

5. A method according to claim 4, wherein said 2-propoxyethanol is in a concentration range from about 0.003% to about 1% (w/v).

6. A method according to claim 1, wherein said non-lysing nonionic surfactant is one selected from the group consisting of polyoxyethylene nonylphenol having from about 30 to about 60 ethylene oxide groups, polyoxyethylene octylphenol having from 30 to about 60 ethylene oxide groups, polyethoxyethylene phosphates having from 30 to about 80 ethylene oxide groups, and polyoxyethylene-polyoxypropylene block copolymer having from about 30 to about 150 ethylene oxide groups and at least 2 propylene oxide groups.

7. A method according to claim 6, wherein said a non-lysing nonionic surfactant is polyoxyethylene nonylphenol having from about 30 to about_60 ethylene oxide group.

8. A method according to claim 6, wherein said polyoxyethylene nonylphenol having from about 30 to about 60 ethylene oxide group is in a concentration range from about 0.003% to about 1% (w/v).

9. A method according to claim 1, wherein the lytic composition further includes an antimicrobial.

10. A method according to claim 1, wherein the lytic reagent composition for differential analysis of leukocytes consists essentially of:
  (a) 2-propoxyethanol in a sufficient amount to preserve leukocytes;
  (b) polyoxyethylene nonylphenol having from about 30 to about 60 ethylene oxide group; and
  (c) an inorganic buffer to maintain pH of said lytic reagent composition in a range from about 9.1 to about 10.7.

11. A method according to claim 10, wherein said inorganic buffer is selected from the group consisting of disodium tetraborate decahydrate, dipotassium tetraborate decahydrate, sodium carbonate, sodium bicarbonate, disodium phosphate, dipotassium phosphate, trisodium phosphate, tripotassium phosphate and mixtures thereof.

12. A method according to claim 11, wherein said inorganic buffer is disodium tetraborate decahydrate.

13. A method according to claim 10, wherein said 2-propoxyethanol is in a concentration range from about 0.003% to about 1% (w/v).

14. A method according to claim 10, wherein said polyoxyethylene nonylphenol having from about 30 to about 60 ethylene oxide group is in a concentration range from about 0.003% to about 1% (w/v).

15. A method according to claim 10, wherein said lytic reagent composition further includes an antimicrobial.

16. A method according to claim 1, wherein said lytic reagent composition enables differentiation of leukocytes into five subpopulations by optical measurements.

17. A method according to claim 16, wherein said five leukocyte subpopulations include neutrophils, lymphocytes, monocytes, eosinophils and basophils.

18. A method according to claim 16, wherein said inorganic buffer is selected from the group consisting of disodium tetraborate decahydrate, dipotassium tetraborate decahydrate, sodium carbonate, sodium bicarbonate, disodium phosphate, dipotassium phosphate, trisodium phosphate, and tripotassium phosphate.

19. A method according to claim 18, wherein said inorganic buffer is disodium tetraborate decahydrate.

20. A method according to claim 16, wherein said short chain alkyl oxyethanol is 2-propoxyethanol.

21. A method according to claim 20, wherein said 2-propoxyethanol is in a concentration range from about 0.003% to about 1% (w/v).

22. A method according to claim 16, wherein said non-lysing nonionic surfactant is one selected from the group consisting of polyoxyethylene nonylphenol having from about 30 to about 60 ethylene oxide groups, polyoxyethylene octylphenol having from 30 to about 60 ethylene oxide groups, polyethoxyethylene phosphates having from 30 to about 80 ethylene oxide groups, and polyoxyethylene-polyoxypropylene block copolymer having from about 30 to about 150 ethylene oxide groups and at least 2 propylene oxide groups.

23. A method according to claim 22, wherein said non-lysing nonionic surfactant is polyoxyethylene nonylphenol having from about 30 to about_60 ethylene oxide group.

24. A method according to claim 23, wherein said polyoxyethylene nonylphenol having from about 30 to about 60 ethylene oxide group is in a concentration range from about 0.003% to about 1% (w/v).

25. A method according to claim 16, wherein the lytic reagent composition further comprises an antimicrobial.

26. A method according to claim 1, wherein said optical measurements comprises multiple angle light scatter measurements and light absorbance measurement.

27. A method according to claim 26, wherein said multiple angle light scatter measurements includes light scatter measurements at from 0° to about 30°, from about 30° to about 50°, and from about 50° to about 90°.

28. A method according to claim 26, wherein said light absorbance measurement is axial light absorbance measurement.

29. A lytic reagent composition for differential analysis of leukocytes consisting essentially of:
  (a) a short chain alkyl oxyethanol selected from the group consisting of 2-methoxyethanol, 2-ethoxyethanol, 2-propoxyethanol, and 2-isopropoxyethanol in a sufficient amount to preserve leukocytes;
  (b) a non-lysing nonionic surfactant as a debris solublizer; and
  (c) disodium tetraborate decahydrate in amount sufficient to maintain pH of said lytic reagent composition in a range from about 9.1 to about 10.7.

30. A lytic reagent composition for differential analysis of leukocytes consisting essentially of:
  (a) 2-propoxyethanol in a sufficient amount to preserve leukocytes;
  (b) polyoxyethylene nonylphenol having from about 30 to about 60 ethylene oxide group; and
  (c) disodium tetraborate decahydrate to maintain pH of said lytic reagent composition in a range from about 9.1 to about 10.7.

31. A lytic reagent composition for differential analysis or leukocytes comprising:
  (a) a short chain alkyl oxyethanol selected from the group consisting of 2-methoxyethanol, 2-ethoxyethanol, 2-propoxyethanol, and 2-isopropoxyethanol in a sufficient amount to preserve leukocytes;
  (b) a non-lysing nonionic surfactant as a debris solublizer; and
  (c) disodium tetraborate decahydrate to maintain pH of said lytic reagent composition in a range from about 9.1 to about 10.7;
  wherein said lytic reagent composition enables differentiation of leukocytes into five subpopulations by optical measurements.

* * * * *